Feb. 12, 1963 L. L. BROOKS Plant Pat. 2,224

AZALEA PLANT

Filed Jan. 8, 1962

INVENTOR
LENARD L. BROOKS

United States Patent Office

Plant Pat. 2,224
Patented Feb. 12, 1963

2,224
AZALEA PLANT

Lenard L. Brooks, 1020 Florence Ave., Modesto, Calif.

Filed Jan. 8, 1962, Ser. No. 165,051
1 Claim. (Cl. 47—60)

Herein is shown and described a new and distinct variety of azalea plant, developed in the experimental section of my nursey at Modesto, California. This azalea plant was produced by using pollen from the kurume azalea Salmon Queen (not patented) on the Belgian indica azalea Jean Haerens (not patented).

Novel characteristics were recognized in the original seedling plant that were an improvement over other varieties of azalea of a similar color and type. Therefore, cuttings were taken for asexual reproduction, and the plants thus produced carried forward all of the novel characteristics of the original seedling plant. The exeprimental asexual reproduction by cuttings was carried out in the experimental section of my nursey at Modesto, California.

This variety of azalea plan is characterized particularly by its rapid, many branched, symmetrical, spreading habit of growth; the ease with which it can be reproduced by cuttings; the habit of setting many multiple flower buds and its high value as a greenhouse forcing or garden variety suitable for areas with a mild climate.

Figure 1:
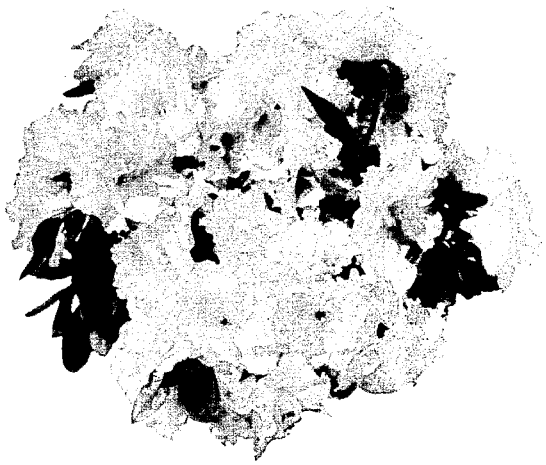
FIGURE 1 shows a young plant in full flower.
Figure 2:
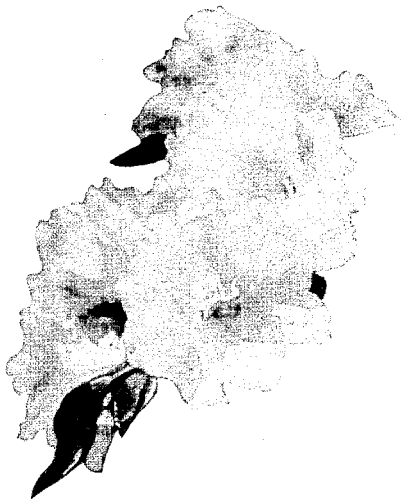
FIGURE 2 shows a single branch with flowers in about two-thirds their normal size.

Referring now more specifically to the botanical details of the new and distinct variety of azalea plant, the following is a more detailed description of the same:

Plant:

*Form.*—Many branched, symmetrical, spreading.

*Growing habit.*—Very dense and bushy with an abundance of large, dark green, light textured leaves.

*Blooming habit.*—Very profuse, flowering evenly over the entire plant when forced in the greenhouse or flowered naturally in the garden.

*Blooming season.*—Plants growing in the outdoor section of my nursey at Modesto, California, bloom naturally in March–April. If pinched at the right time, the plants can be forced for the Christmas market.

Foliage:

*Size.*—Maximum size of mature leaves on young, thrifty plants about three inches long and one and one quarter inches wide, each plant having many smaller leaves.

*Color.*—Growing under good conditions, with an ideal pH value, the mature leaves are a deep shade of fairway green, plate 32–I–12, lighter beneath.

*Shape.*—Ovate, not pointed.

*Aspect.*—Glossy.

*Texture.*—Light.

*Edge.*—Without serrations, some minute hairs.

*Ribs and Veins.*—Normal.

Flower:

*Size.*—Maximum size about 2½ inches wide.

*Form.*—Hose-in-hose, with petaloids in the center that often take the form of a third hose. Rarely, a flower will produce five stamens as found in the normal hose-in-hose azalea flower.

*Borne.*—One to three flowers are produced from each bud. Strong stems often set many buds; twenty-seven flowers having been observed on a single stem. Multi-bud setting is one of the distinguishing features of this variety.

*Permanence.*—Long lasting, holding the color well for the entire life of the flower.

*Color.*—Cosmos pink or deeper under favorable conditions, plate 50–6–D to F.

Reproductive organs:

*Stamens.*—None to five. Most of the stamens that develop are short and ill-shaped, producing no pollen, but infrequently they do reach full maturity and produce pollen.

*Pistil.*—Usually distorted in shaped and poorly developed.

*Ovule.*—Poorly developed.

All color plate identifications refer to a "Dictionary of Color" by Maerz and Paul.

Having thus described and shown the invention, I claim:

A new and distinct variety of azalea plant, substantially as herein shown and described, characterized particularly by its compact, symmertical, spreading habit of growth, its habit of setting many multiple flower buds, its ample dark green foliage, its ease of reproduction by cuttings and its high value as a greenhouse forcing or garden variety for areas having a mild climate.

No references cited.